United States Patent [19]

Nikolaides et al.

[11] Patent Number: 5,395,937
[45] Date of Patent: Mar. 7, 1995

[54] PROCESS FOR PREPARING QUINOLINE AMINES

[75] Inventors: Nick Nikolaides, Woodbury, Minn.; Kyle J. Lindstrom, Houlton, Wis.

[73] Assignee: Minnesota Mining and Manufacturing Company, St. Paul, Minn.

[21] Appl. No.: 11,405

[22] Filed: Jan. 29, 1993

[51] Int. Cl.$^6$ .................. C07D 471/04; C07D 215/20; C07D 215/36; C07D 215/38

[52] U.S. Cl. ........................... 546/82; 546/155; 546/157; 546/159

[58] Field of Search .............. 546/82, 155, 157, 159

[56] References Cited

U.S. PATENT DOCUMENTS

| | | | |
|---|---|---|---|
| 4,689,338 | 8/1987 | Gerster | 514/293 |
| 4,929,624 | 5/1990 | Gerster et al. | 514/293 |
| 4,988,815 | 1/1991 | Andre et al. | 546/159 |

FOREIGN PATENT DOCUMENTS

| | | |
|---|---|---|
| 0385630A2 | 9/1990 | European Pat. Off. |
| 242806 | 2/1987 | Germany |
| 92/06093 | 4/1992 | WIPO |
| 92/15581 | 9/1992 | WIPO |
| 92/15582 | 9/1992 | WIPO |

OTHER PUBLICATIONS

S. Patai, "The Chemistry of Sulphonic Acids, Esters, and Their Derivatives", John Wiley & Sons, pp. 672–678 (1991).
S. Patai, "The Chemistry of the Amino Group", Interscience Publishers, p. 690 (1968).
R. Crossland et al., "Sulfonate Leaving Groups, Structure and Reactivity", Journal of the American Chemical Society, 93:17, pp. 4217–4219 (1971).
J. Heterocyclic Chem. 1988, 25, 857 (Kappe).
J. Heterocyclic Chem. 1977, 14, 813 (Denzel).
J. Med. Chem. 1975, 18, 726 (Buckle et al.).
J. Org. Chem. 1910, 15, 1278 (Bachman et al.).
J. Med. Chem. 1968, 11, 87 (Jain et al.).
Chem. Abs. 1976, 85, 94362z (Baranov et al.).
J. Heterocyclic Chem. 1981, 18, 1537 (Berenyi et al.).

Primary Examiner—Raymond J. Henley, III
Assistant Examiner—Phyllis G. Spivack
Attorney, Agent, or Firm—Gary L. Griswold; Walter N. Kirn; Douglas E. Reedich

[57] ABSTRACT

A process that involves reacting a 3-nitroquinoline-2,4-disulfonate with an amine or a substituted amine to selectively aminate at the 4-position to yield 1H-imidazo[4,5-c]quinolin-4-amines is disclosed.

10 Claims, No Drawings

PROCESS FOR PREPARING QUINOLINE AMINES

BACKGROUND OF THE INVENTION

1. Technical Field

This invention relates to processes for preparing 4-aminoquinolines and to intermediates for use in preparing 4-aminoquinolines. This invention also relates to processes for preparing 1H-imidazo[4,5-c]quinolin-4-amines.

2. Description of the Related Art

Certain antiviral immunomodulator 1H-imidazo[4,5-c]quinolin-4-amines and methods for their preparation are known and disclosed. For example U.S. Pat. Nos. 4,689,338 and 4,929,624 (Gerster) disclose a method involving the step of heating the corresponding 4-chloro compound in the presence of ammonium hydroxide or ammonia under pressure to afford the 4-amino compound. U.S. Pat. No. 4,988,815 (Andre) discloses a process involving amination of the 4-position of a 3-nitro-1,4-dichloroquinoline. This process too involves as a final step the reaction of ammonia with a 4-chloro-1H-imidazo[4,5-c]quinoline.

Milder methods have been used in order to introduce the 4-amino group of 1H-imidazo[4,5-c]quinolin-4-amines. Patent Application PCT WO92/01212 (Gerster) discloses a process involving the reaction of a 1H-imidazo[4,5-c]quinoline 5N-oxide with an organic isocyanate and hydrolysing the product to afford the 4-amino compound. Patent Application PCT WO91/06682 (Gerster) discloses a process involving the reaction of a 1H-imidazo[4,5-c]quinoline 5N-oxide with an acylating agent and reacting the product with an aminating agent to afford the 4-amino compound.

SUMMARY OF THE INVENTION

This invention provides a process for preparing a 1H-imidazo[4,5-c]quinolin-4-amine, comprising the steps of:

(i) providing a 3-nitroquinoline-2,4-disulfonate;

(ii) reacting the compound from step (i) with an amine to afford the 4-(substituted)amino-3-nitroquinoline-2-sulfonate;

(iii) reacting the compound from step (ii) with a hydrogenolyzable amine to afford the 4-(substituted)amino-3-nitroquinoline also substituted at the 2-position with a hydrogenolyzable amino substituent;

(iv) reducing the compound from step (iii) to afford a 3-amino-4-(substituted)aminoquinoline also substituted at the 2-position with a hydrogenolyzable amino substituent;

(v) reacting the compound from step (iv) with a carboxylic acid or an equivalent thereof to provide a (1-substituted) (2-substituted) 1H-imidazo[4,5-c]quinoline also substituted at the 4-position with a hydrogenolyzable amino substituent; and (vi) hydrogenolyzing the compound from step (v) to afford a (1-substituted) (2-substituted) 1H-imidazo[4,5-c]quinolin-4-amine.

This invention also provides processes involving certain of the various individual steps set forth above, and combinations of such steps.

In another aspect this invention also provides 3-nitroquinoline-2,4-disulfonates, 3-nitro-4-(substituted)aminoquinoline-2-sulfonates, 4-(substituted)amino-2-dibenzylamino-3-nitroquinolines, 3-amino-4-(substituted)amino-2-dibenzylaminoquinolines, and (1-substituted) (2-substituted) 1H-imidazo[4,5-c]quinolin-4-dibenzylamines.

DETAILED DESCRIPTION OF THE INVENTION

Substituents designated parenthetically herein indicate that the substituent is optionally present, e.g., a 4-(substituted) amino compound contains either an unsubstituted 4-amino group or a substituted 4-amino group.

The Reaction Scheme illustrates the processes of the invention and the preparation of the compounds of the invention. The unsubstituted compound of Formula I is a known commercially available compound and other compounds of Formula I can be prepared by methods known to those skilled in the art and disclosed, e.g., in *Chem. Ber.* 1927, 60, 1108 (Kohler) and *J. Heterocyclic Chem.* 1988, 25, 857 (Kappe).

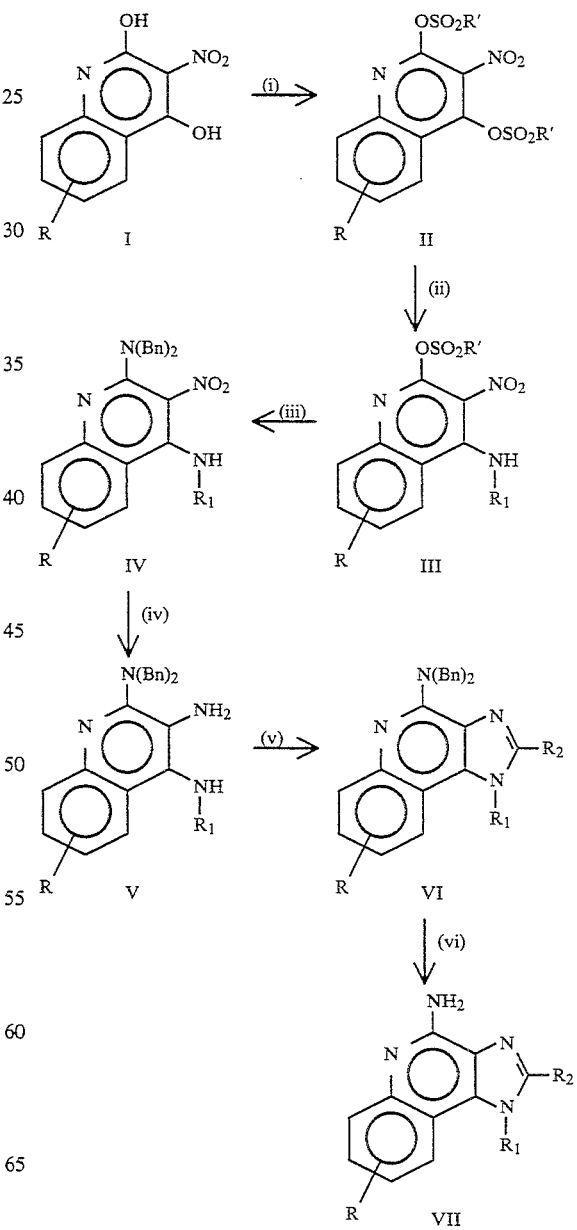

In step (i) a 3-nitroquinoline-2,4-disulfonate is provided by reacting a 2,4-dihydroxy-3-nitroquinoline with a sulfonyl halide or preferably a sulfonic anhydride. Suitable sulfonyl halides include alkylsulfonyl halides such as methanesulfonyl chloride and trifluoromethanesulfonyl chloride, and arylsulfonyl halides such as benzenesulfonyl chloride, p-bromobenzenesulfonyl chloride, and p-toluenesulfonyl chloride. Suitable sulfonic anhydrides include those corresponding to the above-mentioned sulfonyl halides. A particularly preferred sulfonic anhydride is trifluoromethanesulfonic anhydride. Sulfonic anhydrides are preferred in view of the fact that the sulfonate anion generated as a by-product of the reaction is a relatively poor nucleophile and as such does not give rise to undesired side products such as those in which the nitro group has been displaced.

Reaction conditions preferably involve first combining a compound of Formula I with a base, preferably an excess of a tertiary amine base (e.g., a trialkylamine base such as triethylamine) and preferably in an appropriate solvent such as dichloromethane and then adding the sulfonyl halide or the sulfonic anhydride. The addition is preferably carried out in a controlled fashion (e.g., dropwise) and at a reduced temperature (e.g., at about 0° C.). It is notable that the sulfonation reaction of step (i) is generally run at lower temperatures than the corresponding reaction in which the 2,4-dihydroxy-3-nitroquinoline is chlorinated with a chlorinating agent such as phosphorus oxychloride. Thus step (i) more easily avoids formation of side products without the need to carefully control reaction conditions. The product can be isolated by conventional methods or it can be carried on without isolation as described below in connection with step (ii).

Step (ii) of the process of the invention can provide the product 3-nitro-4-(substituted)amino-quinoline-2-sulfonates in essentially quantitative yield from the 2,4-dihydroxy-3-nitroquinoline of Formula I. Despite the presence of two sulfonate groups that could in principle be displaced, the reaction results in selective amination at the 4-position. The compound of Formula II is reacted with an amine, preferably in the presence of an excess of a tertiary amine base in a solvent such as dichloromethane. Suitable amines include ammonia and preferably primary amines, primary amines affording 4-substituted amino compounds of Formula III wherein the amino substituent is represented by $R_1$. A particularly preferred amine is isobutyl amine.

The reaction can be carried out by adding the tertiary amine base to the reaction mixture resulting from step (i), cooling to a reduced temperature (e.g., 0° C.), and adding the amine in a controlled fashion (e.g., dropwise). The reaction can also be carried out by adding the amine to a solution of the compound of Formula II and a tertiary amine base in a solvent such as dichloromethane. As the sulfonate is a relatively facile leaving group the reaction can be run at relatively low temperatures, e.g., about 0° C., in order to decrease the amount of undesired 2-aminated and 2,4-diaminated side products. It is sometimes necessary or desirable to heat the reaction mixture after the addition in order to complete the reaction. The product can be isolated from the reaction mixture by conventional methods.

In step (iii) the compound of Formula III is reacted with a hydrogenolyzable amine to afford a compound of Formula IV. The term "hydrogenolyzable amine" as used herein refers to any amine that is nucleophilic enough to displace the sulfonate group in step (iii) and wherein the substituent or substituents can be removed by hydrogenolysis. Such amines are known to those skilled in the art to include arylmethyl amines and di(arylmethyl)amines, that is, those amines wherein the substituent or substituents are identical or different from one another and with respect to each substituent the amino nitrogen is one carbon removed from an aromatic ring. The term "hydrogenolyzable amino substituent" as used herein refers to the substituent that obtains upon the use of a hydrogenolyzable amine in the reaction of step (iii), i.e., a hydrogenolyzable amine absent one nitrogen-bound hydrogen atom. Primary hydrogenolyzable amines are less preferred, as the resulting product has an alternative site for cyclization in step (v) of the Reaction Scheme. Secondary hydrogenolyzable amines are preferred. Suitable secondary hydrogenolyzable amines include dibenzylamine (i.e., di(phenylmethyl)amine) and substituted derivatives thereof such as di[4-methyl(phenylmethyl)]amine, and other di(arylmethyl)amines such as di(2-furanylmethyl)amine and the like. The Reaction Scheme specifically illustrates the process involving dibenzylamine. However, the process of the invention can be carried out with any suitable hydrogenolyzable amine.

The reaction of step (iii) can be carried out by placing the starting material and the hydrogenolyzable amine in an inert solvent such as benzene, toluene, or xylene, and heating at a temperature and for a time sufficient to cause displacement of the sulfonate group by the hydrogenolyzable amine, such temperature and time being readily selected by those skilled in the art. The product can be isolated from the reaction mixture by conventional methods.

In step (iv) the nitro group of a compound of Formula IV is reduced to an amino group. Methods for such a reduction are well known to those skilled in the art. A preferred method involves in situ generation of $Ni_2B$ from sodium borohydride and $NiCl_2$ in methanol. The compound of Formula IV is added to the reducing agent solution to effect reduction of the nitro group. The product can then be isolated by conventional methods.

In step (v) a compound of Formula V is reacted with a carboxylic acid or an equivalent thereof to afford the cyclized compound of Formula VI. Suitable equivalents to a carboxylic acid include acid halides, orthoesters, and orthoformates, orthoesters, acid halides, and carboxylic acids other than formic acid giving rise to 2-substituted products of Formula VI wherein the 2-substituent is represented by $R_2$. The reaction can be run in the absence of solvent or preferably in an inert solvent such as xylene or toluene in the presence of a carboxylic acid or equivalent with sufficient heating (e.g., at about 80°-150° C. depending on the solvent if any) to drive off any alcohol or water formed as a side product of the reaction.

In step (vi) the cyclized compound of Formula VI is hydrogenolyzed to afford the 4-amino compound. Conventional well known catalytic hydrogenation conditions are suitable. Preferred conditions involve heating in formic acid in the presence of $Pd(OH)_2/C$.

The process of the invention provides as a final product a 1H-imidazo[4,5-c]quinolin-4-amine, preferred embodiments of which can be represented by Formula VII. In the Reaction Scheme generally, R' can be any group that can be incorporated into a sulfonyl halide or a sulfonic anhydride. Alkyl (e.g., methyl), haloalkyl (including perfluoroalkyl, e.g., trifluoromethyl), and aryl, including phenyl, halophenyl and tolyl are all suitable.

Preferably the 1H-imidazo[4,5-c]quinolin-4-amine is a compound defined by one of Formulas XI-XV below:

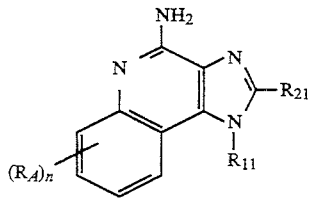

XI wherein $R_{11}$ is selected from the group consisting of alkyl, hydroxyalkyl, acyloxyalkyl, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that if said benzene ring is substituted by two of said moieties, then said moieties together contain no more than 6 carbon atoms; $R_{21}$ is selected from the group consisting of hydrogen, alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that when the benzene ring is substituted by two of said moieties, then the moieties together contain no more than 6 carbon atoms; and each $R_A$ is independently selected from the group consisting of alkoxy of one to about four carbon atoms, halogen and alkyl of one to about four carbon atoms, and n is an integer from 0 to 2, with the proviso that if n is 2, then said $R_A$ groups together contain no more than 6 carbon atoms;

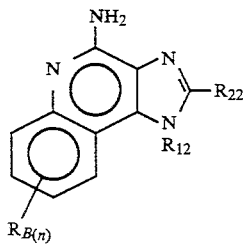

XII wherein $R_{12}$ is selected from the group consisting of straight chain or branched chain alkenyl containing 2 to about 10 carbon atoms and substituted straight chain or branched chain alkenyl containing 2 to about 10 carbon atoms, wherein the substituent is selected from the group consisting of straight chain or branched chain alkyl containing 1 to about 4 carbon atoms and cycloalkyl containing 3 to about 6 carbon atoms; and cycloalkyl containing 3 to about 6 carbon atoms substituted by straight chain or branched chain alkyl containing 1 to about 4 carbon atoms; and $R_{22}$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each $R_B$ is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said $R_B$ groups together contain no more than 6 carbon atoms;

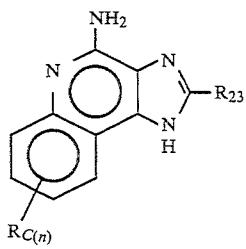

XIII wherein $R_{23}$ is selected from the group consisting of hydrogen, straight chain or branched chain alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to about four carbon atoms, straight chain or branched chain alkoxy of one to about four carbon atoms, and halogen, with the proviso that when the benzene ring is substituted by two such moieties, then the moieties together contain no more than 6 carbon atoms; and each $R_C$ is independently selected from the group consisting of straight chain or branched chain alkoxy of one to about four carbon atoms, halogen, and straight chain or branched chain alkyl of one to about four carbon atoms, and n is an integer from zero to 2, with the proviso that if n is 2, then said $R_C$ groups together contain no more than 6 carbon atoms;

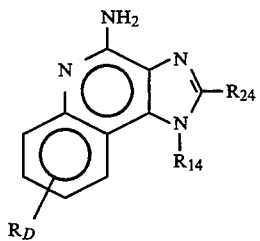

XIV wherein R$_{14}$ —CHR$_x$R$_y$ wherein
R$_y$ is hydrogen or a carbon-carbon bond, with the proviso that when R$_y$ is hydrogen R$_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when R$_y$ is a carbon-carbon bond R$_y$ and R$_x$ together form a tetrahydrofuranyl group optionally substituted with one or more substituents independently selected from the group consisting of hydroxy and hydroxyalkyl of one to about four carbon atoms;
R$_{24}$ is selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and
R$_D$ is selected from the group consisting of hydrogen, straight chain or branched chain alkoxy containing one to about four carbon atoms, halogen, and straight chain or branched chain alkyl containing one to about four carbon atoms;

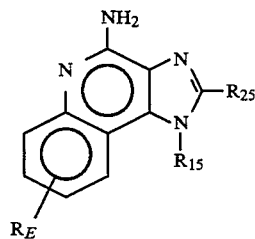

XV wherein
R$_{15}$ is selected from the group consisting of: hydrogen; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;
R$_{25}$ is

wherein
R$_S$ and R$_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;
X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms; and
R$_E$ is selected from the group consisting of hydrogen, straight chain or branched chain alkoxy containing one to about four carbon atoms, halogen, and straight chain or branched chain alkyl containing one to about four carbon atoms;
or a pharmaceutically acceptable salt of any of the foregoing.

The compounds recited above are disclosed and claimed in the several patents and applications noted above in the Summary of the Invention.

In instances where n can be zero, one, or two, n is preferably zero or one.

The substituents R$_A$-R$_E$ above are species embraced by R and are generally designated "benzo substituents" herein. The preferred benzo substituent is hydrogen.

The substituents R$_{11}$-R$_{15}$ above are species embraced by R$_1$ and are generally designated "1-substituents" herein. The preferred 1-substituent is 2-methylpropyl or 2-hydroxy-2-methylpropyl.

The substituents R$_{21}$-R$_{25}$ above are species embraced by R$_2$ and are generally designated "2-substituents" herein. The preferred 2-substituents are hydrogen, alkyl of one to about six carbon atoms, alkoxyalkyl wherein the alkoxy moiety contains one to about four carbon atoms and the alkyl moiety contains one to about four carbon atoms. Most preferably the 2-substituent is hydrogen, methyl, or ethoxymethyl.

Certain benzo substituents, 1-substituents, and 2-substituents will be incompatible with the particular reaction conditions described above in connection with the Reaction Scheme. Those skilled in the art, however, will be able to select alternative conditions under which the several steps can be carried out and/or methods of functional group protection and manipulation that will allow the use of the process of the invention in the preparation of 1H-imidazo[4,5-c]quinolin-4-amines of diverse structures.

Certain 1H-imidazo[4,5-c]quinolin-4-amines have been disclosed as antiviral agents (see, e.g., U.S. Pat. Nos. 4,689,338 (Gerster) and 4,929,624 (Gerster et al.), European Patent Application 90.301776.3 (Gerster), Patent Application PCT WO92/15582 (Gerster et al.), and commonly assigned copending applications, 07/933,408 (Gerster et al.) and 07/788,565 (Gerster et al.) all incorporated herein by reference). Certain of these compounds are also known to induce biosynthesis of cytokines such as interferons, interleukins, and tumor necrosis factor in humans and in mice.

The Examples below are intended to illustrate the invention. All parts and percentages are by weight unless otherwise indicated.

EXAMPLE 1

[4-(2-Methylpropyl)amino-3-nitroquinolin-2-yl]Trifluoromethanesulfonate

Triethylamine (7 mL, 0.05 mole) was added to a suspension of 3-nitro-2,4-quinolinediol (5 g, 0.024 mole) in methylene chloride (150 mL). The resulting solution was cooled to 0° C. in an ice bath and trifluoromethanesulfonic anhydride (8.4 mL, 0.05 mole) was added dropwise using a syringe pump. After the addition was complete, the reaction was refluxed for 10 minutes then once again cooled to 0° C. in an ice bath. Triethylamine (3.5 mL, 0.025 mole) was added to the reaction mixture followed by the addition of isobutylamine (2.9 mL, 0.029 mole). The reaction was heated at reflux for 30 minutes, cooled to ambient temperature, washed with 100 mL of saturated aqueous sodium bicarbonate then dried over magnesium sulfate. The methylene chloride solution was then put through a layer of silica gel and the silica gel was eluted with additional methylene chloride. The methylene chloride solution was evaporated under vacuum to provide a yellow/orange solid. The structure was confirmed by nuclear magnetic resonance spectroscopy. Mass spectroscopy showed m/z equal to 393. Analysis: Calculated for $C_{14}H_{14}F_3N_3O_5S$: % C, 42.74; % H, 3.59; % N, 10.68; Found: % C, 42.42; % H, 3.45; % N, 10.49.

EXAMPLE 2

$N^2,N^2$-Bis(phenylmethyl)-$N^4$-(2-methylpropyl)-3-nitroquinoline-2,4-diamine

Dibenzylamine (7.2 g, 0.037 mole) was added to a solution of [4-(2-methylpropyl)amino-3-nitroquinolin-2-yl] trifluoromethanesulfonate (6.8 g, 0.017 mole, Example 1) in toluene (200 mL) and the reaction mixture was refluxed for 90 minutes. The toluene was evaporated under vacuum to provide a red oil. The oil was taken up in methylene chloride (100 mL). The methylene chloride solution was washed with aqueous saturated sodium bicarbonate (100 mL), dried over magnesium sulfate then put through a layer of silica gel. The silica gel was eluted with additional methylene chloride to remove all of the red colored material. The eluant was concentrated under vacuum to provide an oil. The oil was taken up in hexane/methylene chloride and placed on a layer of silica gel. The silica gel was eluted with 10–20 percent methylene chloride in hexane. The eluant was concentrated under vacuum to provide a red oil which solidified on standing. The structure was confirmed by nuclear magnetic resonance spectroscopy. Mass spectroscopy showed m/z equal to 440. Analysis: Calculated for $C_{27}H_{28}N_4O_2$: % C, 73.61; % H, 6.41, % N, 12.72. Found: % C, 72.99; % H, 6.38; % N, 12.40.

EXAMPLE 3

$N^2,N^2$-Bis(phenylmethyl)-$N^4$-(2-methylpropyl)quinoline-2,3,4-triamine Hydrochloride Sodium borohydride (0.78 g, 20 mmole) was carefully added to a solution containing nickel(II) chloride hydrate (1.6 g, 6.8 mmole) in methanol (180 mL) and stirred at ambient temperature for 30 minutes. $N^2,N^2$-bis(phenylmethyl)-$N^4$-(2-methylpropyl)-3-nitroquinoline-2,4-diamine (6 g, 13.6 mmole, Example 2) was taken up in a mixture of methylene chloride (50 mL) and methanol (20 mL) and added to the nickel borate reagent. Sodium borohydride (1.5 g) was added and the reaction color changed from orange to colorless and a black precipitate formed. The reaction mixture was filtered through a layer of celite and the filtrate concentrated under vacuum. The residue was partitioned between methylene chloride (200 mL) and water (200 mL) and the layers separated. The aqueous layer was extracted with additional methylene chloride. The methylene chloride extracts were combined, dried over magnesium sulfate and concentrated under vacuum. The residue was taken up in diethyl ether, combined with concentrated hydrochloric acid (1.2 mL, 1 equivalent) and stirred for 1 hour. The yellow precipitate was isolated by filtration and dried to provide 4 g of the desired product. The structure was confirmed by nuclear magnetic resonance spectroscopy.

EXAMPLE 4

N,N-Bis(phenylmethyl)-1-(2-methylpropyl)-1H-imidazo[4,5-c]quinolin-4-amine $N^2,N^2$-Bis(phenylmethyl)-$N^4$-(2-methylpropyl)-quinoline-2,3,4-triamine (2.7 g, Example 3) was combined with triethylorthoformate (12 mL) and heated until the temperature reached 80° C. The reaction mixture was cooled then diluted with ether and filtered to provide 2.4 g of the hydrochloride salt of the desired product. The salt was suspended in ether then combined with aqueous sodium bicarbonate. The layers were separated. The ether layer was dried then evaporated to provide 1.9 g of the desired product. The structure was confirmed by nuclear magnetic resonance spectroscopy.

EXAMPLE 5

1-(2-Methylpropyl)-1H-imidazo[4,5-c]quinolin-4-amine

Palladium hydroxide on carbon, Pearlman's catalyst, (0.25 g) was added to a solution containing N,N-bis(phenylmethyl)-1-(2-methylpropyl)-1H-imidazo[4,5-c]quinolin-4-amine (0.4 g, 0.95 mmole, Example 4) in formic acid (20 mL). The reaction was heated at reflux for about 16 hours at which time more catalyst (0.2 g) was added and heating was continued until the reaction was complete as indicated by thin layer chromatography (silica gel; 5% methanol in methylene chloride). The reaction mixture was diluted with water (20 mL), methylene chloride (40 mL) and methanol (10 mL) then filtered. The filtrate layers were separated and the organic layer was concentrated under vacuum. The residue was recrystallized from dimethyl formamide then suspended in methanol and stirred before being isolated by filtration and dried to provide 0.1 g of a solid. The melting point and spectral properties of this material matched those of an authentic sample.

EXAMPLE 6

[4-(2-Methylpropyl)amino-3-nitroquinolin-2-yl]Methanesulfonate

Triethylamine (70.5 mL, 0.075 mole) was added to a suspension of 3-nitro-2,4-quinolinediol (5 g, 0.024 mole) in methylene chloride (150 mL). The resulting solution was cooled in an ice bath and methanesulfonyl chloride (3.9 mL, 0.05 mole) was added dropwise. The reaction mixture was heated at reflux for 15 minutes then once again cooled in an ice bath. Isobutylamine (2.9 mL, 0.029 mole) was added and the reaction mixture was heated at reflux for 30 minutes before being allowed to cool to ambient temperature. The reaction mixture was washed with water and saturated aqueous sodium bicarbonate, dried over magnesium sulfate then put through a silica gel column. The eluant was concentrated under vacuum to provide 1.2 g of the desired product. The structure was confirmed by nuclear magnetic resonance spectroscopy.

EXAMPLE 7

$N^2,N^2$-Bis(phenylmethyl)-$N^4$-(2-methylpropyl)-3-nitroquinoline-2,4-diamine

Triethylamine (0.4 mL, 2.9 mmole) and dibenzylamine (0.62 mL, 3.2 mmole) were added to a solution containing [4-(2-methylpropyl)amino-3-nitroquinolin-2-yl] methanesulfonate (1.0 g, 2.9 mmole, Example 6) in toluene (35 mL). The reaction mixture was heated at reflux for 24 hours then concentrated under vacuum. The residue was purified by silica gel chromatography eluting with methylene chloride to provide a red oil. This oil was purified by silica gel chromatography eluting with 5% ethyl acetate in hexane to provide 0.4 g of the desired product as a red oil. The structure was confirmed by nuclear magnetic resonance spectroscopy.

EXAMPLE 8

3-Nitro-2,4-bis[(trifluoromethyl)sulfonyloxy]quinoline

Triethylamine (1.35 mL, 9.7 mmole) was added to a suspension of 3-nitro-2,4-quinolinediol (1 g, 4.8 mmole) in methylene chloride (50 mL). The resulting solution was cooled to 0° C. in an ice bath and trifluoromethanesulfonic anhydride (1.63 mL, 9.7 mmole) was added dropwise. After the addition was complete the reaction mixture was allowed to warm to ambient temperature over a period of 2 hours. The reaction mixture was washed twice with water (40 mL), dried over magnesium sulfate then filtered through a 2 inch thick layer of silica gel. The filter cake was flushed with additional methylene chloride (100 mL). The filtrate was concentrated under vacuum to provide an oil. The oil was recrystallized from hexane and treated with activated charcoal to provide 1.57 g of the desired product as an off-white solid, m.p. 74.5°–76° C. Analysis: Calculated for $C_{11}H_4F_6N_2O_8S_2$: % C, 28.09; % H, 0.86; % N, 5.96; Found: % C, 28.12; % H, 0.83; % N, 5.91.

We claim:

1. A process for preparing a 4-(substituted)amino-3-nitroquinoline-2-sulfonate comprising the steps of:
   (i) providing a 3-nitroquinoline-2,4-disulfonate;
   (ii) reacting the compound from step (i) with an amine to provide a 4-(substituted)amino-3nitroquinoline-2-sulfonate.

2. A process for preparing a 4-(substituted)amino-3-nitroquinoline substituted at the 2-position with a hydrogenolyzable amino substituent, comprising the steps of:
   (i) providing a 3-nitroquinoline-2,4-disulfonate;
   (ii) reacting the compound from step (i) with an amine to provide a 4-(substituted)amino-3-nitroquinoline-2-sulfonate; and
   (iii) reacting the compound from step (ii) with a hydrogenolyzable amine to provide a 4-(substituted)amino-3-nitroquinoline substituted at the 2-position with a hydrogenolyzable amino substituent.

3. A process for preparing a 3-amino-4-(substitute)aminoquinoline substituted at the 2-position with a hydrogenolyzable amino substituent comprising the steps of:
   (i) providing a 3-nitroquinoline-2,4-disulfonate;
   (ii) reacting the compound from step (i) with an amine to provide a 4-(substituted)amino-3-nitroquinoline-2-sulfonate;
   (iii) reacting the compound from step (ii) with a hydrogenolyzable amine to provide a 4-(substituted)amino-3-nitroquinoline substituted at the 2-position with a hydrogenolyzable amino substituent; and
   (iv) reducing the compound from step (iii) to provide a 3-amino-4-(substituted)aminoquinoline substituted at the 2-position with a hydrogenolyzable amino substituent.

4. A process for preparing a (1-substituted) (2-substituted) 1H-imidazo[4,5-c]-quinoline substituted at the 4-position with a hydrogenolyzable amino substituent, comprising the steps of:
   (i) providing a 3-nitroquinoline-2,4-disulfonate;
   (ii) reacting the compound from step (i) with an amine to provide a 4-(substituted)amino-3-nitroquinoline-2-sulfonate;
   (iii) reacting the compound from step (ii) with a hydrogenolyzable amine to provide a 4-(substituted)amino-3-nitroquinoline substituted at the 2-position with a hydrogenolyzable amino substituent;
   (iv) reducing the compound from step (iii) to provide a 3-amino-4-(substituted)aminoquinoline substituted at the 2-position with a hydrogenolyzable amino substituent; and
   (v) reacting the compound from step (iv) with a carboxylic acid or an equivalent thereof to provide a (1-substituted) (2-substituted) 1H-imidazo[4,5-c]quinoline substituted at the 4-position with a hydrogenolyzable amino substituent.

5. A process for preparing a (1-substituted) (2-substituted) 1H-imidazo[4,5-c]-quinolin-4-amine, comprising the steps of:
   (i) providing a 3-nitroquinoline-2,4-disulfonate;
   (ii) reacting the compound from step (i) with an amine to provide a 4-(substituted)amino-3-nitroquinoline-2-sulfonate;
   (iii) reacting the compound from step (ii) with a hydrogenolyzable amine to provide a 4-(substituted- )amino-3-nitroquinoline substituted at the 2-position with a hydrogenolyzable amino substituent;

(iv) reducing the compound from step (iii) to provide a 3-amino-4-(substituted)aminoquinoline substituted at the 2-position with a hydrogenolyzable amino substituent;

(v) reacting the compound from step (iv) with a carboxylic acid or an equivalent thereof to provide a (1-substituted) (2-substituted) 1H-imidazo[4,5-c]quinoline substituted at the 4-position with a hydrogenolyzable amino substituent; and (vi) hydrogenolyzing the compound from step (v) to provide a (1-substituted) (2-substituted) 1H-imidazo[4,5-c]quinolin-4-amine.

6. A compound selected from the group consisting of 3-nitro-2,4-bis [(trifluoromethyl)sulfonyloxy]quinoline and 3-nitro-2,4-bis(methylsulfonyloxy)quinoline.

7. A compound selected from the group consisting of [4-(2-methylpropyl)amino-3-nitroquinolin-2-yl]trifluoromethanesulfonate, [4-(2-hydroxy-2-methylpropyl)amino-3-nitroquinolin-2-yl]trifluoromethanesulfonate, [4-(2-methylpropyl)amino-3-nitroquinolin-2-yl]methanesulfonate, and [4-(2-hydroxy-2-methylpropyl)amino-3-nitroquinolin-2yl]methanesulfonate.

8. A compound selected from the group consisting of $N^2,N^2$-Bis(phenylmethyl)-$N^4$-(2-methylpropyl)-3-nitroquinoline-2,4-diamine and $N^2,N^2$-bis(phenylmethyl)-$N^4$-(2-hydroxy-2-methylpropyl)-3-nitroquinoline-2,4-diamine.

9. A compound selected from the group consisting of $N^2,N^2$-bis (phenylmethyl)-$N^4$-(2-methylpropyl )quinoline-2,3,4-triamine and $N^2,N^2$-bis(phenylmethyl)-$N^4$-(2-hydroxy-2-methylpropyl)quinoline-2,3,4-triamine.

10. A compound selected from the group consisting of N,N-bis(phenylmethyl)-1-(2-methylpropyl)-1H-imidazo[4,5-c]quinolin-4-amine and N,N-bis(phenylmethyl)-1-(2-hydroxy-2-methylpropyl)-1H-imidazo[4,5-c]quinolin-4-amine.

* * * * *